United States Patent [19]

Ishizumi et al.

[11] 3,991,048
[45] Nov. 9, 1976

[54] PROCESS FOR THE PREPARATION OF 1,4-BENZODIAZEPINE DERIVATIVES

[75] Inventors: Kikuo Ishizumi, Toyonaka; Kazuo Mori, Kobe; Shigeho Inaba, Takarazuka; Hisao Yamamoto, Kobe, all of Japan

[73] Assignee: Sumitomo Chemical Company, Limited, Osaka, Japan

[22] Filed: Feb. 25, 1975

[21] Appl. No.: 552,888

[30] Foreign Application Priority Data
Feb. 27, 1974 Japan.............................. 49-24622

[52] U.S. Cl........................ 260/239.3 D; 424/244; 260/453 AL; 260/570 AB
[51] Int. Cl.² .................................... C07D 243/28
[58] Field of Search............................ 260/239.3 D

[56] References Cited
UNITED STATES PATENTS
3,371,085  2/1968  Reeder et al. ............. 260/239.3 D Primary Examiner—Henry R. Jiles
Assistant Examiner—Robert T. Bond
Attorney, Agent, or Firm—Stevens, Davis, Miller & Mosher

[57] ABSTRACT

A 1,4-benzodiazepine derivative, or a pharmaceutically acceptable acid salt thereof, of the formula,

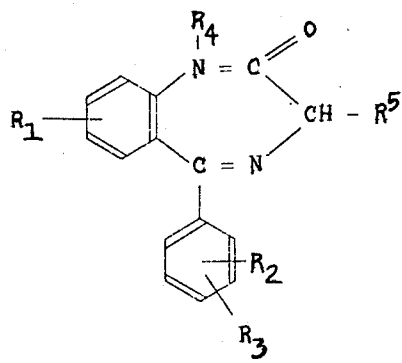

wherein $R_1$ is hydrogen, halogen, nitro or trifluoromethyl; $R_2$ and $R_3$ are independently hydrogen, halogen, lower alkyl or trifluoromethyl; $R_4$ is lower alkyl, alkenyl, trihaloalkyl, alkoxyalkyl, alkenyloxyalkyl, alkoxyalkoxyalkyl, alkanoyloxyalkyl, cycloalkylalkyl, alkylthioalkyl, alkylsulfinylalkyl, alkylsulfonylalkyl or a group of the formula

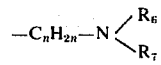

in which $R_6$ and $R_7$ are independently lower alkyl, and $n$ is an integer of 1 to 4; and $R_5$ is hydrogen or lower alkyl, is obtained by reacting a benzophenone derivative of the formula,

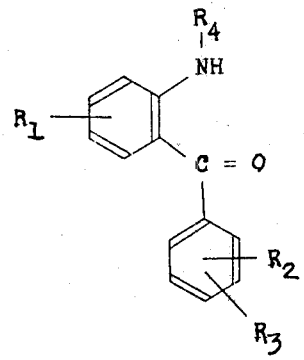

wherein $R_1$, $R_2$, $R_3$ and $R_4$ are as defined above, with a 2-isocyanatoacetyl chloride derivative of the formula

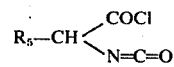

wherein $R_5$ is as defined above.

3 Claims, No Drawings

PROCESS FOR THE PREPARATION OF 1,4-BENZODIAZEPINE DERIVATIVES

This invention relates to a novel process for the preparation of benzodiazepine derivatives and salts thereof. More particularly, the invention pertains to a novel process for preparing benzodiazepine derivatives, and pharmaceutically acceptable acid addition salts thereof, of the general formula (1),

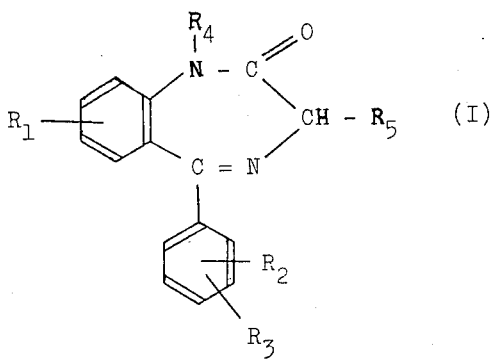

wherein $R_1$ is hydrogen, halogen, nitro or trifluoromethyl; $R_2$ and $R_3$ are independently hydrogen, halogen, lower alkyl or trifluoromethyl; $R_4$ is lower alkyl, alkenyl, trihaloalkyl, alkoxyalkyl, alkenyloxyalkyl, alkoxyalkoxyalkyl, alkanoyloxyalkyl, cycloalkylalkyl, alkylthioalkyl, alkylsulfinylalkyl, alkylsulfonylalkyl or a group of the formula

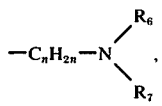

in which $R_6$ and $R_7$ are independently lower alkyl, and $n$ is an integer of 1 to 4; and $R_5$ is hydrogen or lower alkyl.

In the compound of the above-mentioned formula (I), the halogen includes fluorine, chlorine, bromine and iodine; the expression alkyl represents a straight chain or branched-chain alkyl group; the lower alkyl includes $C_1$ to $C_4$ alkyl groups such as, for example, methyl, ethyl, n-propyl, isopropyl, n-butyl, isobutyl and tert-butyl groups; the cycloalkyl includes $C_3$ to $C_6$ cycloalkyl groups such as, for example, cyclopropyl, cyclobutyl and cyclopentyl groups; the trihaloalkyl includes, for example, trichloromethyl, trifluoromethyl and trifluoroethyl groups; and the alkenyl includes $C_2$ to $C_5$ alkenyl groups such as, for example, vinyl, allyl, propenyl and butenyl groups. The meanings of the terms alkyl and alkenyl explained in the above are the same also in the cases of the alkyl moieties of the other terms employed for the definition of the formula (I) such as, for example, alkoxyalkyl, alkenyoxyalkyl, alkanoyloxyalkyl and alkylthioalkyl. Further, the alkylene group represented by the formula $C_nH_{2n}$ is a straight chain or branched-chain alkylene group having 1 to 4 carbon atoms, and includes, for example, methylene, ethylene, 1-methylethylene, 2-methylethylene, trimethylene, 1-methyltrimethylene and 2-methyltrimethylene groups.

The benzodiazepine derivatives represented by the formula (I) which are obtained by the process of the present invention have strong central nervous depressing actions such as, for example, strong tranquilizing, muscle-relaxing, anti-convulsive and hypnotic actions, and hence are quite useful as tranquilizer.

Several processes have heretofore been known as to the synthesis of benzodiazepine derivatives represented by the formula (I). One of the most general among these is a process in which a benzophenone derivative of the formula (II).

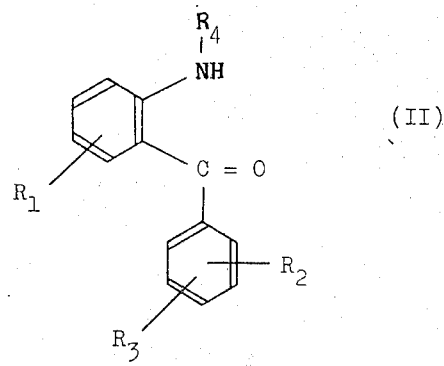

wherein $R_1$, $R_2$, $R_3$ and $R_4$ are as defined previously, is reacted with a halogenoacetyl halide, and the resulting halogenoacetanilide derivative is reacted with ammonia to synthesize a benzodiazepine derivative of the formula (I). This synthesis process, however, has such disadvantage that if $R_1$ in the formula (II) is an electron-attracting group such as a nitro group, the reaction of the halogenoacetanilide derivative with ammonia leads to a rearrangement of the Smiles reaction type to give an anilinoacetamide derivative, and thus no desired benzodiazepine derivative of the formula (I) can be obtained [refer to J. Org. Chem., 38, 373 (1973)].

As a result of extensive studies, the present inventors have found a more general process for synthesizing benzodiazepine derivatives in which a benzophenone derivative of the aforesaid formula (II) is used as the starting material and, even when $R_1$ in the formula (II) is a nitro group, the desired benzodiazepine derivative of the formula (I) can be obtained. Based on the above finding, the inventors have accomplished the present invention.

The process of the present invention is simple in reaction operation, and is markedly advantageous when practiced on commercial scale.

Accordingly, an object of the present invention is to provide an improved process for preparing a benzodiazepine derivative of the formula (I) as defined above.

Other objects and advantages of the invention will become apparent from the following description.

In accordance with the present invention, there is provided a process for preparing a benzodiazepine derivative of the aforesaid formula (I) by reacting a benzophenone derivative of the aforesaid formula (II) with a 2-isocyanatoacetyl chloride derivative of the formula (III),

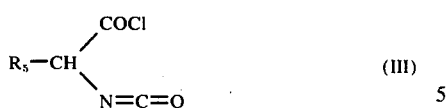

wherein $R_5$ is as defined previously, and ring-closing the said benzophenone derivative to obtain the benzodiazepine derivative.

The reaction of the benzophenone derivative of the formula (II) with the 2-isocyanatoacetyl chloride derivative of the formula (III) proceeds smoothly either in a solvent or by using the 2-isocyanatoacetyl chloride derivative in excess in place of the solvent. Examples of the solvent used in this case include chloroform, carbon tetrachloride, methylene chloride, dichloroethane, ether, tetrahydrofuran, dioxane, pyridine and a mixture thereof. The reaction progresses at a low temperatures, in general, but may, if necessary, be carried out at a temperature up to the reflux temperature of the solvent.

The ring-closing reaction for converting an intermediate compound formed by the above-mentioned reaction to the benzodiazepine derivative of the formula (I) proceeds by merely dissolving the intermediate compound at room temperature in a solvent such as alcohol, chloroform or methylene chloride, but may also be conducted by heating the system in the presence or absence of a solvent. Examples of the solvent used in this case include chloroform, carbon tetrachloride, acetone, tetrahydrofuran, methylene chloride, benzene, toluene, xylene, alcohol, pyridine, dimethyl formamide and dimethyl sulfoxide. In practicing the present process, the benzodiazepine derivative of the formula (I) may, if desired, be obtained by one step without isolating the intermediate compound.

The benzodiazepine derivative obtained in the above-mentioned process may be taken up also as an acid addition salt by treatment with an acid, e.g. a mineral acid such as hydrochloric, sulfuric, nitric or phosphoric acid, or an organic acid such as maleic, fumaric, succinic, formic or acetic acid.

The 2-isocyanatoacetyl chloride derivative of the formula (III), which is another starting compound used in the present invention, may be easily synthesized according to, for example, the process disclosed in J. Org. Chem., 30, 1158 (1965).

According to the process of the present invention, there are prepared, for example, the following benzodiazepine derivatives:

1-Methyl-5-(o-fluorophenyl)-1,3-dihydro-2H-1,4-benzodiazepin-2-one.
1-Cyclopropylmethyl-5-(o-fluorophenyl)-7-chloro-1,3-dihydro-2H-1,4-benzodiazepin-2-one
1-Methyl-5-phenyl-7-trifluoromethyl-1,3-dihydro-2H-1,4-benzodiazepin-2-one
1-Methyl-5-(o-fluorophenyl)-7-nitro-1,3-dihydro-2H-1,4-benzodiazepin-2-one
1,3-Dimethyl-5-phenyl-1,3-dihydro-2H-1,4-benzodiazepin-2-one
1-($\beta$-Vinyloxyethyl)-5-phenyl-7-chloro-1,3-dihydro-2H-1,4-benzodiazepin-2-one
1-($\beta$-Methoxy-$\beta$-ethoxyethyl)-5-phenyl-7-chloro-1,3-dihydro-2H-1,4-benzodiazepin-2-one
1-($\beta$-Acetoxyethyl)-5-phenyl-7-chloro-1,3-dihydro-2H-1,4-benzodiazepin-2-one
1-($\beta$-Methylthioethyl)-5-phenyl-7-chloro-1,3-dihydro-2H-1,4-benzodiazepin-2-one
1-($\beta$-Methylsulfinylethyl)-5-phenyl-7-chloro-1,3-dihydro-2H-1,4-benzodiazepin-2-one
1-($\beta$-Methylsulfonylethyl)-5-phenyl-7-chloro-1,3-dihydro-2H-1,4-benzodiazepin-2-one 1-Methyl-5-(o,o'-difluorophenyl)-7-chloro-1,3-dihydro-2H-1,4-benzodiazepin-2-one
1-Methyl-5-phenyl-7-bromo-1,3-dihydro-2H-1,4-benzodiazepin-2-one
1-Methyl-5-(o-fluorophenyl)-7-nitro-1,4-dihydro-2H-1,4-benzodiazepin-2-one
1-Allyl-5-phenyl-7-chloro-1,3-dihydro-2H-1,4-benzodiazepin-2-one
1-($\beta,\beta,\beta$-Trifluoroethyl)-5-phenyl-7-chloro-1,3-dihydro-2H-1,4-benzodiazepin-2-one
1-($\beta$-Methoxyethyl)-5-(o-fluorophenyl)-7-chloro-1,3-dihydro-2H-1,4-benzodiazepin-2-one
1-($\beta$-Ethoxyethyl)-5-(o-fluorophenyl)-7-chloro-1,3-dihydro-2H-1,4-benzodiazepin-2-one
1-Methoxymethyl-5-phenyl-7-chloro-1,3-dihydro-2H-1,4-benzodiazepin-2-one
1-Cyclopropylmethyl-5-phenyl-7-chloro-1,3-dihydro-2H-1,4-benzodiazepin-2-one
1-($\beta$-Dimethylaminoethyl)-5-(o-fluorophenyl)-7-chloro-1,3-dihydro-2H-1,4-benzodiazepin-2-one
1-($\beta$-Diethylaminoethyl)-5-(o-fluorophenyl)-7-chloro-1,3-dihydro-2H-1,4-benzodiazepin-2-one The present invention is illustrated in detail below with reference to examples, but it is needless to say that the examples are merely by way of illustration and not by way of limitation.

EXAMPLE 1

1. Into a solution of 2.0 g. of 2-isocyanatoacetyl chloride in 15 ml. of dry ether, 3.42 g. of 2-methylamino-5-chlorobenzophenone was dropped at 3° to 7° C. with ice-cooling and stirring. The resulting mixture was stirred at 1° to 3° C. for 3.5 hours to deposit crystals, which were then recovered by filtration and washed with dry ether to obtain 4.95 g. of a compound having a melting point of 110° to 114° C. (decomp.).

Infrared absorption spectrum: 3320, 1760, 1680, 1660, 1600 cm$^{-1}$.

| Elementary analysis (for $C_{17}H_{14}O_3N_2Cl_2$): | | | | |
|---|---|---|---|---|
| | C | H | N | Cl |
| Calculated (%) | 55.91 | 3.86 | 7.67 | 19.41 |
| Found (%) | 56.07 | 3.95 | 7.78 | 19.48 |

2. 1.0 Gram of the compound obtained in the above-mentioned (1) was dissolved in 10 ml. of dry pyridine, and the resulting solution was refluxed for 10 hours. After removing pyridine in the reaction liquid by reduced pressure distillation, the residue was chromatographically purified (solvent: ethyl acetate) by use of a column packed with 50 g. of silica gel to obtain 1-methyl-5-phenyl-7-chloro-1,3-dihydro-2H-1,4-benzodiazepin-2-one having a melting point of 127° to 130° C.

EXAMPLE 2

Example 1-(2) was repeated, except that the solvent pyridine was replaced by toluene and the reflux was conducted for 4.5 hours, to obtain 1-methyl-5-phenyl- 7-chloro-1,3-dihydro-2H-1,4-benzodiazepin-2-one having a melting point of 127° to 130° C.

EXAMPLE 3

0.10 Gram of the compound obtained in Example 1-(1) was dissolved in 10 ml of methylene chloride, and the resulting solution was stirred at room temperature for 8 hours. Subsequently, the methylene chloride was removed by reduced pressure distillation, and the residue was chromatographically purified (solvent: ethyl acetate) by use of a column packed with 5 g. of silica gel to obtain 1-methyl-5-phenyl-7-chloro-1,3-dihydro-2H-1,4-benzodiazepin-2-one.

EXAMPLE 4

Example 3 was repeated, except that the solvent methylene chloride was replaced by ethanol, to obtain 1-methyl-5-phenyl-7-chloro-1,3-dihydro-2H-1,4-benzodiazepin- 2-one.

EXAMPLE 5

2-Milliliters of 2-isocyanatoacetyl chloride was cooled, and 0.20 g. of powdered 2-methylamino-5-nitrobenzophenone was added thereto with stirring. After stirring the resulting mixture at room temperature for one hour, excess 2-isocyanatoacetyl chloride was removed by reduced pressure distillation. To the residue was added 4 ml. of pyridine, whereby a reaction took place with generation of heat. The reaction liquid was heated at 95° C, for 1.5 hours, diluted with water and then extracted with chloroform. The chloroform layer was washed with a 5% aqueous hydrochloric acid solution and then with an aqueous sodium chloride solution in this order, dried over Glauber's salt, and evaporated by reduced pressure distillation. Subsequently, the residue was chromatographically purified (solvent: chloroform   ethyl acetate) by use of a column packed with 10 g. of silica gel to obtain 1-methyl-5-phenyl-7-nitro-1,3-dihydro-2H-1,4-benzodiazepin-2-one having a melting point of 154° to 156° C.

EXAMPLE 6

To 0.2 g. of 2-($\beta,\beta,\beta$-trifluoroethylamino)-5-chlorobenzophenone was added 0.76 g. of 2-isocyanatoacetyl chloride, and the resulting mixture was heated and reacted at 42° to 48° C. for 2 hours with stirring. After removing excess 2-isocyanatoacetyl chloride by reduced pressure distillation, the oily residue was dissolved in 1 ml. of dimethyl sulfoxide, and the resulting solution was stirred at room temperature and then at 57° to 60° C. for 2 hours. Subsequently, the reaction liquid was poured into 20 ml. of water to deposit crystals, which were then recovered by filtration, washed with water, and then chromatographically purified (solvent: chloroform) by use of a column packed with 20 g. of silica gel to obtain 0.144 g. of 1-($\beta,\beta,\beta$-trifluoroethyl)-5-phenyl-7-chloro-1,3-dihydro-2H-1,4-benzodiazepin-2-one having a melting point of 160° to 163° C.

What is claimed is:
1. A process for producing a compound of the formula (I) and its non-toxic, pharmaceutically acceptable acid addition salt,

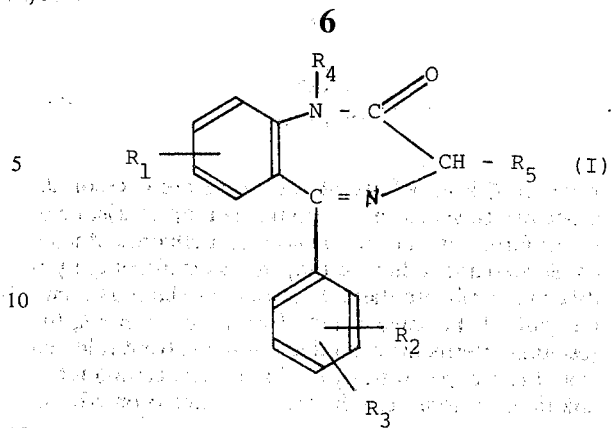

wherein $R_1$ is hydrogen, halogen, nitro or trifluoromethyl; $R_2$, $R_3$ are independently hydrogen, halogen, $C_1$—$C_4$ alkyl or trifluoromethyl; $R_4$ is $C_1$—$C_4$ alkyl, $C_2$—$C_5$ alkenyl, trihalo($C_1$—$C_4$)alkyl, $C_1$—$C_4$ alkoxy($C_1$—$C_4$)alkyl, $C_2$—$C_5$ alkenyloxy-($C_1$—$C_4$)alkyl, $C_1$—$C_4$ alkoxy($C_1$—$C_4$)alkoxy($C_1$—$C_4$)alkyl, $C_2$—$C_5$ alkanoyloxy($C_1$—$C_4$)alkyl, $C_3$—$C_6$ cycloalkyl($C_1$—$C_4$)alkyl, $C_1$—$C_4$ alkylthio($C_1$—$C_4$) alkyl, $C_1$—$C_4$ alkylsulfinyl($C_1$—$C_4$)alkyl, $C_1$—$C_4$ alkylsulfonyl($C_1$—$C_4$)alkyl or a group of the formula

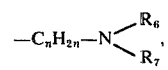

in which $R_6$ and $R_7$ are independently $C_1$—$C_4$ alkyl, and $n$ is an integer of 1 to 4; and $R_5$ is hydrogen or $C_1$—$C_4$ alkyl, which comprises reacting a compound of the formula (II),

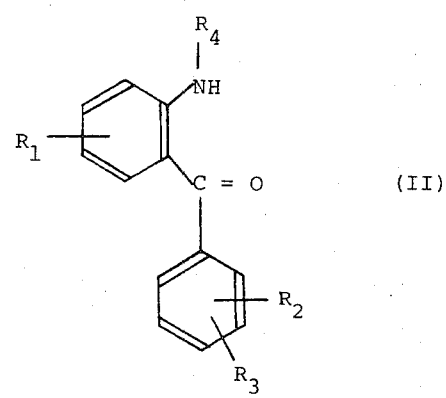

wherein $R_1$, $R_2$, $R_3$ and $R_4$ are as defined above, with a compound of the formula (III),

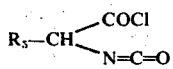 (III)

wherein $R_5$ is as defined above, in the presence or absence of a solvent selected from the group consisting of chloroform, carbon tetrachloride, dichloromethane, dichloroethane, ether, tetrahydrofuran, dioxane, pyridine and a mixture thereof at or below the reflux temperature of the solvent and, if necessary, treating the resulting intermediate product with a solvent selected from the group consisting of chloroform, carbon tetrachloride, acetone, tetrahydrofuran, dichloromethane, benzene, toluene, xylene, ethanol, pyridine, dimethyl formamide and dimethyl sulfoxide at or below the reflux temperature of the solvent.

2. A process according to claim 1, wherein the reaction is carried out by cyclizing an intermediate compound formed by the reaction between a compound of the formula (II) and a compound of the formula (III).

3. A process according to claim 1, wherein the reaction is carried out without isolating an intermediate compound formed by the reaction between the compound of the formula (II) with the compound of the formula (III).

* * * * *